United States Patent [19]
Curtze et al.

[11] Patent Number: 6,127,570
[45] Date of Patent: Oct. 3, 2000

[54] FUNGICIDAL SUBSTITUTED 2-HYDROXYBENZOPHENONES

[75] Inventors: Juergen Curtze, Geisenheim; Gerd Morschhaeuser, Gau-Algesheim, both of Germany; Henry Van Tuyl Cotter, Trenton, N.J.

[73] Assignee: American Cyanamid Company, Madison, N.J.

[21] Appl. No.: 09/329,712

[22] Filed: Jun. 10, 1999

[51] Int. Cl.⁷ .................................................. C07L 69/00
[52] U.S. Cl. ......................... 560/140; 560/130; 568/533; 562/474; 574/546; 574/548; 574/568; 574/718
[58] Field of Search .................................... 560/140, 130; 562/474; 568/533; 514/546, 548, 568, 718

[56] References Cited

U.S. PATENT DOCUMENTS 3,924,002 12/1975 Duennenberger et al. .
5,679,866 10/1997 Curtze et al. .

FOREIGN PATENT DOCUMENTS

93/02036 2/1993 WIPO .

OTHER PUBLICATIONS

Islam, et al., J. Chem. Res. Miniprint 2, 1991, pp.367–378.

*Primary Examiner*—Paul J. Killos
*Attorney, Agent, or Firm*—Barbara L. Renda

[57] ABSTRACT

Substituted 2-hydroxybenzophenone compounds are disclosed, having the formula:

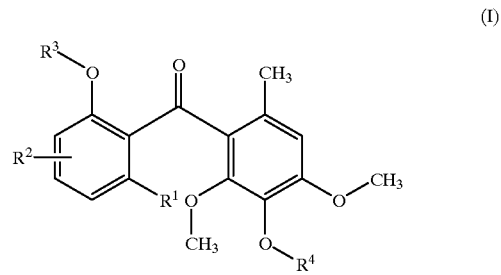

(I)

The compounds are useful as fungicides having high systemicities.

16 Claims, No Drawings

FUNGICIDAL SUBSTITUTED 2-HYDROXYBENZOPHENONES

BACKGROUND OF THE INVENTION

This invention relates to certain 2-hydroxybenzophenone compounds, a process for their preparation, compositions containing such compounds, a method for combating a fungus at a locus comprising treating the locus with such compounds and their use as fungicides.

Food production relies upon a variety of agricultural technologies to ensure the growing population's dietary needs remain affordable, nutritious and readily available on grocery store shelves. Fungicides are one of these agricultural technologies which are available to the world community. Fungicides are agrochemical compounds which protect crops and foods from fungus and fungal diseases. Crops and food are constantly threatened by a variety of fungal organisms, which, if left uncontrolled, can cause ruined crops and devastated harvests.

In particular, ascomycetes, the causative agent for powdery mildew diseases are an ever-present threat especially to cereal and fruit crops. However, applications of fungicidal agents at disease control rates can cause phytotoxic damage to the target plants.

Similar benzophenone compounds are disclosed in a general formula of European patent application EP 0 727 141. The EP application discloses compounds having activity against phytopathogenic fungi, but relatively low systemicity. However, there is no hint to substituted 2-hydroxybenzophenones.

U.S. Pat. No. 3,924,002 discloses 2-hydroxybenzophenones substituted by up to 4 groups selected from halogen, alkyl, cycloalkyl or phenyl for combating harmful microorganisms such as bacteria and fungi. However, there is no hint to alkoxy-substituted benzophenones. Moreover, there is no indication that alkoxy-substituted 2-hydroxybenzophenones could be highly active against phytopathogenic fungi, in particular against ascomycetes, the causative agent for powdery mildew diseases.

SUMMARY OF THE INVENTION

The present invention provides a compound of formula I (I)

wherein
$R^1$ represents a halogen atom, an alkyl or fluoroalkyl group;
$R^2$ represents a hydrogen or halogen atom, or an optionally substituted alkyl or alkoxy group or a nitro group; or
$R^1$ and $R^2$ may be taken together to represent a —CH=CH—CH=CH— group;
$R^3$ represents a hydrogen atom or a protecting group; and
$R^4$ represents an optionally substituted alkyl group.

The compounds combine excellent selective fungicidal activities in various crops with high systemicities.

It is an object of the present invention to provide highly systemic fungicidal compounds.

It is also an object of the invention to provide methods for controlling an undesired fungus by contacting said plants with a fungicidally effective amount of the compounds.

It is another object of the invention to provide selective fungicidal compositions containing the compounds as active ingredients.

These and other objects and features of the invention will be more apparent from the detailed description set forth hereinbelow, and from the appended claims.

DETAILED DESCRIPTION OF THE PREFERRED EMBODIMENTS

It has surprisingly been found that the compounds of formula I (I)

in which $R^1$ through $R^4$ have the meaning given above combine excellent fungicidal activity against phytopathogenic fungi, in particular those that cause powdery mildew diseases and have comparably high systemicity.

In general terms, unless otherwise stated, as used herein the term halogen atom may denote a bromine, iodine, chlorine or fluorine atom, and is especially a bromine, chlorine or fluorine atom, in particular a bromine or chlorine atom.

Optionally substituted moieties may be unsubstituted or have from one up to the maximal possible number of substituents. Typically, 0 to 2 substituents are present. Each optionally substituted group independently is substituted by one or more halogen atoms or nitro, cyano, cycloalkyl, preferably $C_{3-6}$ cycloalkyl, cycloalkenyl, preferably $C_{3-6}$ cycloalkenyl, haloalkyl, preferably $C_{1-6}$ haloalkyl, halocycloalkyl, preferably $C_{3-6}$ halocycloalkyl, alkoxy, preferably $C_{1-6}$ alkoxy, haloalkoxy, preferably $C_{1-6}$ haloalkoxy, phenyl, halo- or dihalo-phenyl or pyridyl groups.

In general terms, unless otherwise stated herein, the terms alkyl and alkoxy as used herein with respect to a radical or moiety refer to a straight or branched chain radical or moiety. As a rule, such radicals have up to 10, in particular up to 6 carbon atoms. Suitably an alkyl or alkoxy moiety has from 1 to 6 carbon atoms, preferably from 1 to 5 carbon atoms. A preferred alkyl moiety is the methyl, ethyl, n-propyl, isopropyl or n-butyl group.

In general terms, unless otherwise stated herein, the term fluoroalkyl as used herein with respect to a radical or moiety refers to a straight or branched chain radical or moiety. As a rule, such radicals have up to 10, in particular up to 6 carbon atoms. Suitably a fluoroalkyl moiety has from 1 to 6 carbon atoms, preferably from 1 or 2 carbon atoms. The fluoroalkyl groups include alkyl groups in which one or more, in particular all hydrogen atoms have been replaced by fluorine. A preferred fluoroalkyl moiety is represented by the formula —(CH$_2$)$_m$—(CF$_2$)$_n$—Y, in which m is 0, 1 or 2, n is 1, 2, 3, 4 or 5 and Y represents a hydrogen or fluoro atom. Particularly preferred is the difluoromethyl, trifluoromethyl, 2,2,2-trifluoroethyl, pentafluoroethyl, or n-heptafluoropropyl, group.

In general terms, unless otherwise stated herein, the term protecting group as used herein with respect to radical R$^3$ refers to a group which is easily cleaved off without affecting the alkoxy groups present, preferably an easily hydrolyzable group such as ester groups derived from organic acids such as alkanoic acids or from inorganic acids such as sulfuric acid or phosphoric acid, or trihydrocarbylsilyl groups such as trimethylsilyl or tert-butyl-dimethylsilyl groups. Preferred protecting groups are optionally substituted acyl groups, in particular C$_{2-6}$ alkanoyl groups.

Particularly preferred are such protecting groups which are cleaved off after the compound has been applied to the plants.

The invention especially relates to compounds of the general formula I in which any alkyl part of the groups R$^1$, R$^2$ and R$^4$, which may be straight chained or branched, contains up to 10 carbon atoms, preferably up to 9 carbon atoms, more preferably up to 6 carbon atoms, and in which each optionally substituted group independently is substituted by one or more halogen atoms or nitro, cyano, cycloalkyl, preferably C$_{3-6}$ cycloalkyl, cycloalkenyl, preferably C$_{3-6}$ cycloalkenyl, haloalkyl, preferably C$_{1-6}$ haloalkyl, halocycloalkyl, preferably C$_{3-6}$ halocycloalkyl, alkoxy, preferably C$_{1-6}$ alkoxy, haloalkoxy, preferably C$_{1-6}$ haloalkoxy, phenyl, or pyridyl groups, in which the phenyl moiety is optionally substituted by one or two substituents selected from halogen atoms, cyano, C$_{1-6}$ alkyl and C$_{1-6}$ alkoxy groups.

The invention especially relates to compounds of the general formula I in which R$^1$ represents a halogen atom, in particular chlorine, a straight-chained or branched C$_{1-10}$ alkyl, in particular a straight-chained C$_{1-3}$ alkyl group, most preferably being a methyl group.

The invention especially relates to compounds of the general formula I in which R$^2$ represents a hydrogen or halogen atom, in particular a chlorine, bromine or iodine atom, a nitro, a C$_{1-10}$ alkyl or a C$_{1-10}$ haloalkyl group, most preferred being a hydrogen, chlorine or bromine atom. If R$^2$ is different from hydrogen, it is most preferred attached in the ortho-position to radical R$^1$.

The invention especially relates to compounds of the general formula I in which R$^3$ represents a hydrogen atom or a C$_1$–C$_6$ acyl group, preferably a C$_2$–C$_5$ acyl group, in particular a acetyl or pivaloyl group.

The invention especially relates to compounds of the general formula I in which R$^4$ represents an optionally substituted straight-chained or branched C$_{1-5}$ alkyl, in particular a straight-chained C$_{1-3}$ alkyl group, most preferably an unsubstituted or substituted methyl group. This methyl group is preferably unsubstituted or substituted by a phenyl group which is unsubstituted or substituted by one to five, preferably one or two halogen atoms or C$_{1-4}$ alkyl or C$_{1-4}$ alkoxy groups.

The 2-hydroxybenzophenone compounds according to formula I are oils, gums, or, predominantly, crystalline solid materials and possess valuable fungicidal properties. For example, they can be used in agriculture, or related fields such as horticulture and viticulture, for the control of phytopathogenic fungi, especially ascomycetes, in particular powdery mildew diseases such as those caused by *Blumeria (Erysiphe) graminis, Erysiphe cichoracearum, Podosphaera leucotricha, Uncinula necator* and the like. Said 2-hydroxybenzophenone compounds possess a high fungicidal activity over a wide concentration range and may be used in agriculture without harmful phytotoxic effects.

Moreover, the compounds according to the invention show enhanced residual control of fungi and fungal diseases such as cereal, cucumber, apple and grape powdery mildew, and improved foliar systemicity compared with conventional fungicides.

Useful results in terms of control of phytopathogenic fungi are obtained with a compound as defined in formula I wherein:

R$^1$ represents a chloro atom or a methyl group, in particular a methyl group;

R$^2$ represents a hydrogen, chloro or bromo atom or a methyl group, in particular a bromo atom;

R$^3$ represents a hydrogen atom or a C$_{2-6}$ acyl group; in particular a hydrogen atom or an acetyl or pivaloyl group; and R$^4$ represents a C$_{1-5}$ alkyl group, in particular a methyl group.

If R$^2$ represents Cl or Br, it is preferably attached to the benzene ring in the ortho-position with respect to radical R$^1$.

In particular the compounds of formula IA are preferred:

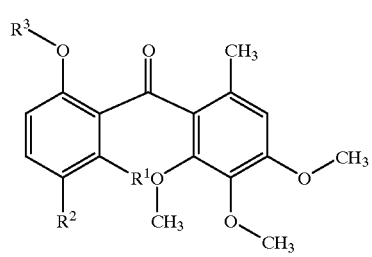

(IA)

in which

R$^1$ represents a chloro atom or a methyl group,

R$^2$ represents a hydrogen, chloro or bromo atom or a methyl or trifluoromethyl group, and R$^3$ represents a hydrogen atom or an acetyl or pivaloyl group.

Especially good results in terms of control of phytopathogenic fungi are obtained by using, for example, the following compounds of formula I:

6,6'-dimethyl-2-hydroxy-2',3',4'-trimethoxy-benzophenone,
6,6'-dimethyl-2-acetoxy-2',3',4'-trimethoxy-benzophenone,
5-bromo-6,6'-dimethyl-2-hydroxy-2',3',4'-trimethoxy-benzophenone,
5-bromo-6,6'-dimethyl-2-acetoxy-2',3',4'-trimethoxy-benzophenone,
5-bromo-6,6'-dimethyl-2-pivaloyloxy-2',3',4'-trimethoxy-benzophenone,
5-chloro-6,6'-dimethyl-2-hydroxy-2',3',4'-trimethoxy-benzophenone,
5-chloro-6,6'-dimethyl-2-acetoxy-2', 3', 4'-trimethoxy-benzophenone,
5-bromo-6,6'-dimethyl-2-pivaloyloxy-2',3', 4'-trimethoxy-benzophenone.

The present invention provides a process for the preparation of a compound of formula I, which comprises reacting a compound of formula II,

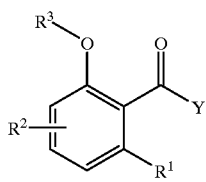

(II)

wherein $R^1$, $R^2$ and $R^3$ have the meaning given above and Y represents a leaving group, in particular a chloro atom or a hydroxy group, with compound of formula III,

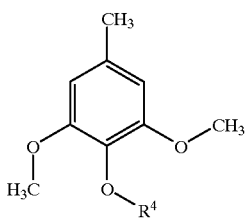

(III)

wherein $R^4$ has the meaning given for claim 1; in the presence of a Lewis acid, preferably phosphorous pentoxide.

The present invention further provides a process for the preparation of a compound of formula I, which comprises the steps of (a) reacting a compound of formula II,
wherein $R^1$ and $R^2$ have the meaning given above and $R^3$ represents a hydrogen atom, and Y represents a hydroxy group, with phosgene in the presence of a base to obtain an intermediate of formula

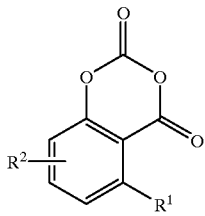

(b) reacting said intermediate with a compound of formula III, wherein $R^4$ has the meaning given for claim 1; in the presence of a Lewis acid.

The compounds of formula II, wherein $R^2$ represents a halogen atom, are preferably obtained by a process which comprises the steps of (a) reacting a compound of formula IV,

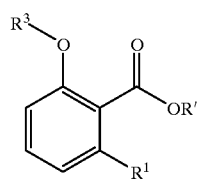

(IV)

wherein $R^1$ and $R^3$ have the meaning given for claim 1 and R' represents a hydrogen atom or an alkyl group, with a halogenating agent, (b) optionally hydrolyzing the resulting halogenated alkyl benzoate (R'=alkyl), and (c) optionally treating the resulting halogenated benzoic acid with thionyl chloride.

In a further process according to the present invention the compounds of formula I are prepared by reacting a compound of formula II, wherein Y represents a chloro atom and $R^3$ represents a protecting group, with a Grignard reagent of formula V,

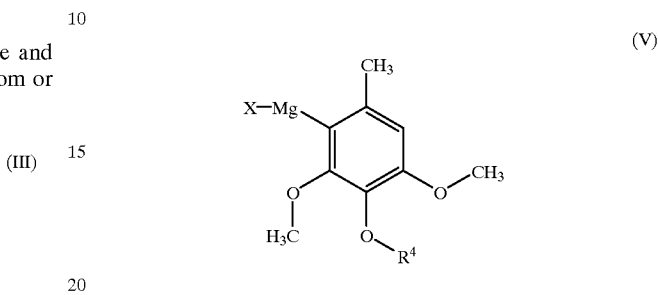

(V)

wherein $R^4$ has the meaning given and X represents a halogen atom.

The starting materials of formulae III, IV and V are known products, the starting materials of formula II are partly known and partly novel products.

Accordingly, the invention provides novel intermediates of formula IIA

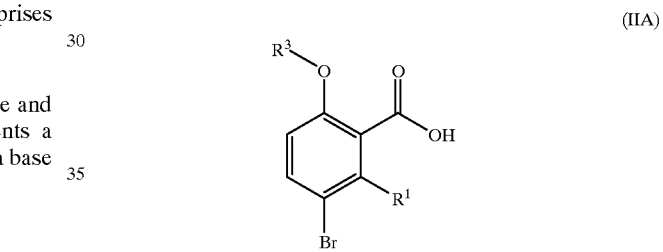

(IIA)

wherein $R^1$ represents a chloro atom or an alkyl group, in particular a methyl group and $R^3$ represents a hydrogen atom, an acetyl or pivaloyl group.

The starting materials of formulae III, IV and V may be prepared according to established methods or routine adaptations thereof. Substituents which are not compatible with the selected reaction conditions may be introduced after formation of the benzophenone. They may be generated by known methods such as subsequent derivatization or substitution of a suitable group or by cleaving off a suitable protecting group.

The Friedel Crafts reaction between formula II and III is effected in the presence of a Lewis acid catalyst according to well-established procedures.

In a preferred process according to the invention the Friedel Crafts reaction between the compound of formula II, wherein $R^3$ is a hydrogen atom, and Y represents a hydroxy group, and the compound of formula III is carried out in the presence of phosgene (W. H Davies, J. Chem. Soc. 1951, 1357) or oxalyldichloride and $AlCl_3$.

In another preferred process according to the invention the benzoic acid of formula II (Y=OH) is reacted with a compound of formula III in the presence of phosphorous pentoxide at temperatures of about 0 to 50° C., preferably at room temperature.

The Grignard reaction between the compound of formula V and the compound of formula II, wherein $R^3$ represents a protecting group and Y is a chloro atom, is as a rule carried out in the presence of an inert diluent as for example disclosed by M. Renson et al., Bull. Soc. Chim. Bel. 69, 236 (1960).

The halogenation of the benzoate of formula IV is preferably carried out in the presence of an inert solvent. Preferred halogenating agents are for example sulfuryl chloride, bromine and N-halosuccininimides such as N-iodo-succinimide. If R' represents a halogen atom highly polar solvents such as alcohols or carboxylic acids, in particular acetic acid are preferred. If $R^1$ represents an alkyl group, in particular a methyl group, non-polar solvents such as tetrachloromethane are preferred. If the reaction is carried out with bromine at a temperature between 0 and 40° C., preferably at room temperature, the halogenation takes place predominately in the ortho-position with respect to radical $R_1$.

In a preferred embodiment the compounds of formula II, in which $R^2$ represents a bromo atom are prepared by reacting a compound of formula VI, wherein $R^1$ represents an alkyl group, n is 0, and R' represents a hydrogen atom, with bromine. This bromination step is preferably carried out in the presence of a polar, protic solvent, such as an aliphatic alcohol or an aliphatic carboxylic acid, in particular acetic acid. The bromination may be carried out advantageously in the presence of a weak base or a buffer system, such as sodium acetate or sodium carbonate.

A preferred embodiment of the process of the instant invention is a process wherein bromine is employed in an amount selected from a value in the range between 1.0 to 1.5, in particular 1.05 to 1.2 molar equivalents with respect to starting compound of formula VI.

The reaction between the compound of formula VI and bromine is as a rule carried out at a temperature sufficient to optimally convert the compound of formula VI to the compound of formula III. This term represents a temperature sufficiently high to maintain the conversion, but also sufficiently low to avoid decomposition of the starting material and the product. The reaction is carried out preferably at temperatures between 0° C. and 40° C., in particular at ambient temperature.

The reaction between the compound of formula VI and bromine is as a rule carried out at a length of time sufficient to optimally convert the compound of formula VI to the compound of formula III. This term represents a period of time sufficiently long to convert the maximum amount of the starting material to the compound of formula III. The reaction is carried out preferably at reaction time between 1 and 40 hours, in particular between 5 and 24 hours.

The processes described below can analogously be applied to other starting compounds, if desired.

Due to excellent plant tolerance, the compounds of formula I may be used in cultivation of all plants where infection by the controlled fungi is not desired, e.g. cereals, vegetables, legumes, apples, vine. The absence of target crop phytotoxicity at fungus control rates is a feature of the present invention.

The compounds of general formula I have been found to have fungicidal activity. Accordingly, the invention further provides a fungicidal composition which comprises an active ingredient, which is at least one compound of formula I as defined above, and one or more carriers. A method of making such a composition is also provided which comprises bringing a compound of formula I as defined above into association with the carrier(s). Such a composition may contain a single active ingredient or a mixture of several active ingredients of the present invention. It is also envisaged that different isomers or mixtures of isomers may have different levels or spectra of activity and thus compositions may comprise individual isomers or mixtures of isomers.

A composition according to the invention preferably contains from 0.5% to 95% by weight (w/w) of active ingredient.

A carrier in a composition according to the invention is any material with which the active ingredient is formulated to facilitate application to the locus to be treated, which may for example be a plant, seed or soil, or to facilitate storage, transport or handling. A carrier may be a solid or a liquid, including material which is normally a gas but which has been compressed to form a liquid.

The compositions may be manufactured into e.g. emulsion concentrates, solutions, oil in water emulsions, wettable powders, soluble powders, suspension concentrates, dusts, granules, water dispersible granules, micro-capsules, gels and other formulation types by well-established procedures. These procedures include intensive mixing and/or milling of the active ingredients with other substances, such as fillers, solvents, solid carriers, surface active compounds (surfactants), and optionally solid and/or liquid auxiliaries and/or adjuvants. The form of application such as spraying, atomizing, dispersing or pouring may be chosen like the compositions according to the desired objectives and the given circumstances.

Solvents may be aromatic hydrocarbons, e.g. Solvesso® 200, substituted naphthalenes, phthalic acid esters, such as dibutyl or dioctyl phthalate, aliphatic hydrocarbons, e.g. cyclohexane or paraffins, alcohols and glycols as well as their ethers and esters, e.g. ethanol, ethyleneglycol mono- and dimethyl ether, ketones such as cyclohexanone, strongly polar solvents such as N-methyl-2-pyrrolidone, or γ-butyrolactone, higher alkyl pyrrolidones, e.g. n-octylpyrrolidone or cyclohexylpyrrolidone, epoxidized plant oil esters, e.g. methylated coconut or soybean oil ester and water. Mixtures of different liquids are often suitable.

Solid carriers, which may be used for dusts, wettable powders, water dispersible granules, or granules, may be mineral fillers, such as calcite, talc, kaolin, montmorillonite or attapulgite. The physical properties may be improved by addition of highly dispersed silica gel or polymers. Carriers for granules may be porous material, e.g. pumice, kaolin, sepiolite, bentonite; non-sorptive carriers may be calcite or sand. Additionally, a multitude of pre-granulated inorganic or organic materials may be used, such as dolomite or crushed plant residues.

Pesticidal compositions are often formulated and transported in a concentrated form which is subsequently diluted by the user before application. The presence of small amounts of a carrier which is a surfactant facilitates this process of dilution. Thus, preferably at least one carrier in a composition according to the invention is a surfactant. For example, the composition may contain at two or more carriers, at least one of which is a surfactant.

Surfactants may be nonionic, anionic, cationic or zwitterionic substances with good dispersing, emulsifying and wetting properties depending on the nature of the compound according to general formula I to be formulated. Surfactants may also mean mixtures of individual surfactants.

The compositions of the invention may for example be formulated as wettable powders, water dispersible granules, dusts, granules, solutions, emulsifiable concentrates, emulsions, suspension concentrates and aerosols. Wettable powders usually contain 5 to 90% w/w of active ingredient and usually contain in addition to solid inert carrier, 3 to 10% w/w of dispersing and wetting agents and, where necessary, 0 to 10% w/w of stabilizer(s) and/or other additives such as penetrants or stickers. Dusts are usually formulated as a dust concentrate having a similar composition to that of a wettable powder but without a dispersant, and may be diluted in the field with further solid carrier to give a composition usually containing 0.5 to 10% w/w of active ingredient. Water dispersible granules and granules are usually prepared to have a size between 0.15 mm and 2.0 mm and may be manufactured by a variety of techniques. Generally, these types of granules will contain 0.5 to 90% w/w active ingredient and 0 to 20% w/w of additives such as stabilizer, surfactants, slow release modifiers and binding agents. The so-called "dry flowables" consist of relatively small granules having a relatively high concentration of active ingredient. Emulsifiable concentrates usually contain, in addition to a solvent or a mixture of solvents, 1 to 80% w/v active ingredient, 2 to 20% w/v emulsifiers and 0 to 20% w/v of other additives such as stabilizers, penetrants and corrosion inhibitors. Suspension concentrates are usually milled so as to obtain a stable, non-sedimenting flowable product and usually contain 5 to 75% w/v active ingredient, 0.5 to 15% w/v of dispersing agents, 0.1 to 10% w/v of suspending agents such as protective colloids and thixotropic agents, 0 to 10% w/v of other additives such as defoamers, corrosion inhibitors, stabilizers, penetrants and stickers, and water or an organic liquid in which the active ingredient is substantially insoluble; certain organic solids or inorganic salts may be present dissolved in the formulation to assist in preventing sedimentation and crystalization or as antifreeze agents for water.

Aqueous dispersions and emulsions, for example compositions obtained by diluting the formulated product according to the invention with water, also lie within the scope of the invention.

Of particular interest in enhancing the duration of the protective activity of the compounds of this invention is the use of a carrier which will provide slow release of the pesticidal compounds into the environment of a plant which is to be protected.

The biological activity of the active ingredient can also be increased by including an adjuvant in the spray dilution. An adjuvant is defined here as a substance which can increase the biological activity of an active ingredient but is not itself significantly biologically active. The adjuvant can either be included in the formulation as a coformulant or carrier, or can be added to the spray tank together with the formulation containing the active ingredient.

As a commodity the compositions may preferably be in a concentrated form whereas the end user generally employs diluted compositions. The compositions may be diluted to a concentration down to 0.001% of active ingredient. The doses usually are in the range from 0.01 to 10 kg a.i./ha.

Examples of formulations according to the invention are:

Emulsion Concentrate (EC)

| | | |
|---|---|---|
| Active Ingredient | Compound of Example 2 | 30% (w/v) |
| Emulsifier(s) | Atlox ® 4856 B/ | 5% (w/v) |
| | Atlox ® 4858 B [1] | |
| | (mixture containing calcium alkyl aryl sulfonate, fatty alcohol ethoxylates and light aromatics/ mixture containing calcium alkyl aryl sulfonate, fatty alcohol ethoxylates and light aromatics) | |
| Solvent | Shellsol ® A [2] | to 1000 ml |
| | (mixture of $C_9$–$C_{10}$ aromatic hydrocarbons) | |

Suspension Concentrate (SC)

| | | |
|---|---|---|
| Active Ingredient | Compound of Example 2 | 50% (w/v) |
| Dispersing agent | Soprophor ® FL [3] | 3% (w/v) |
| | (polyoxyethylene polyaryl phenyl ether phosphate amine salt) | |
| Antifoaming agent | Rhodorsil ® 422 [3] | 0.2% (w/v) |
| | (nonionic aqueous emulsion of polydimethylsiloxanes) | |
| Structure agent | Kelzan ® S [4] | 0.2% (w/v) |
| | (Xanthan gum) | |
| Antifreezing agent | Propylene glycol | 5% (w/v) |
| Biocidal agent | Proxel ® [5] | 0.1% (w/v) |
| | (aqueous dipropylene glycol solution containing 20% 1,2-benisothiazolin-3-one) | |
| Water | | to 1000 ml |

Wettable Powder (WP)

| | | |
|---|---|---|
| Active Ingredient | Compound of Example 2 | 60% (w/w) |
| Wetting agent | Atlox ® 4995 [1] | 2% (w/w) |
| | (polyoxyethylene alkyl ether) | |
| Dispersing agent | Witcosperse ® D-60 [6] | 3% (w/w) |
| | (mixture of sodium salts of condensed naphthalene sulfonic acid and alkylarylpolyoxy acetates | |
| Carrier/Filler | Kaolin | 35% (w/w) |

Water Dispersible Granules (WG)

| | | |
|---|---|---|
| Active Ingredient | Compound of Example 2 | 50% (w/w) |
| Dispersing/ | Witcosperse ® D-450 6) | 8% (w/w) |
| Binding agent | (mixture of sodium salts of condensed naphthalene sulfonic acid and alkyl sulfonates) | |
| Wetting agent | Morwet ® EFW [6] | 2% (w/w) |
| | (formaldehyde condensation product) | |
| Antifoaming agent | Rhodorsil ® EP 6703 [3] | 1% (w/w) |
| | (encapsulated silicone) | |
| Disintegrant | Agrimer ® ATF [7] | 2% (w/w) |
| | (cross-linked homopolymer of N-vinyl-2-pyrrolidone) | |
| Carrier/Filler | Kaolin | 35% (w/w) |

[1] available from ICI Surfactants
[2] available from Deutsche Shell AG
[3] available from Rhône-Poulenc
[4] available from Kelco Co
[5] available from Zeneca
[6] available from Witco
[7] available from International Speciality Products The compositions of this invention can also comprise other compounds having biological activity, e.g. compounds having similar or complementary pesticidal activity or compounds having plant growth regulating, herbicidal or insecticidal activity. These mixtures of pesticides can have a broader spectrum of activity than the compound of general formula I alone. Furthermore, the other pesticide can have a synergistic effect on the pesticidal activity of the compound of general formula I.

The compositions of this invention can comprise also other compounds having biological activity, e.g. compounds having similar or complementary fungicidal activity or compounds having plant growth regulating, herbicidal or insecticidal activity.

The other fungicidal compound can be, for example, one which is capable of combating diseases of cereals (e.g. wheat) such as those caused by Erysipha, Puccinia, Septoria, Gibberella and Helminthosporium spp., seed and soil borne diseases and downy and powdery mildews on vines and powdery mildew and scab on apples etc. These mixtures of fungicides can have a broader spectrum of activity than the compound of general formula I alone.

Examples of the other fungicidal compounds are anilazine, azoxystrobin, benalaxyl, benomyl, binapacryl, bitertanol, blasticidin S, Bordeaux mixture, bromuconazole, bupirimate, captafol, captan, carbendazim, carboxin, carpropamid, chlorbenzthiazon, chlorothalonil, chlozolinate, copper-containing compounds such as copper oxychloride, and copper sulfate, cycloheximide, cymoxanil, cypofuram, cyproconazole, cyprodinil, dichlofluanid, dichlone, dichloran, diclobutrazol, diclocymet, diclomezine, diethofencarb, difenoconazole, diflumetorim, dimethirimol, dimethomorph, diniconazole, dinocap, ditalimfos, dithianon, dodemorph, dodine, edifenphos, epoxiconazole, etaconazole, ethirimol, etridiazole, famoxadone, fenapanil, fenarimol, fenbuconazole, fenfuram, fenhexamid, fenpiclonil, fenpropidin, fenpropimorph, fentin, fentin acetate, fentin hydroxide, ferimzone, fluazinam, fludioxonil, flumetover, fluquinconazole, flusilazole, flusulfamide, flutolanil, flutriafol, folpet, fosetyl-aluminium, fuberidazole, furalaxyl, furametpyr, guazatine, hexaconazole, imazalil, iminoctadine, ipconazole, iprodione, isoprothiolane, kasugamycin, kitazin P, kresoxim-methyl, mancozeb, maneb, mepanipyrim, mepronil, metalaxyl, metconazole, methfuroxam, myclobutanil, neoasozin, nickel dimethyldithiocarbamate, nitrothalisopropyl, nuarimol, ofurace, organo mercury compounds, oxadixyl, oxycarboxin, penconazole, pencycuron, phenazineoxide, phthalide, polyoxin D, polyram, probenazole, prochloraz, procymidione, propamocarb, propiconazole, propineb, pyrazophos, pyrifenox, pyrimethanil, pyroquilon, pyroxyfur, quinomethionate, quinoxyfen, quintozene, spiroxamine, SSF-126, SSF-129, streptomycin, sulfur, tebuconazole, tecloftalame, tecnazene, tetraconazole, thiabendazole, thifluzamide, thiophanate-methyl, thiram, tolclofosmethyl, tolylfluanid, triadimefon, triadimenol, triazbutil, triazoxide, tricyclazole, tridemorph, triflumizole, triforine, triticonazole, validamycin A, vinclozolin, XRD-563, zarilamid, zineb, ziram.

In addition, the formulations according to the invention may contain at least one benzophenone of formula I and any of the following classes of biological control agents such as viruses, bacteria, nematodes, fungi, and other microorganism which are suitable to control insects, weeds or plant diseases or to induce host resistance in the plants. Examples of such biological control agents are: *Bacillus thuringiensis, Verticillium lecanii, Autographica californica NPV, Beauvaria bassiana, Ampelomyces quisqualis, Bacilis subtilis, Pseudomonas fluorescens, Steptomyces griseoviridis* and *Trichoderma harzianum.*

Moreover, the co-formulations according to the invention may contain at least one benzophenone of formula I and a chemical agent that induces the systemic acquired resistance in plants such as for example isonicotinic acid or derivatives thereof, 2,2-dichloro-3,3-dimethylcyclopropanecarboxylic acid or BION.

The compounds of general formula I can be mixed with soil, peat or other rooting media for the protection of the plants against seed-borne, soil-borne or foliar fungal diseases.

The invention still further provides the use as a fungicide of a compound of the general formula I as defined above or a composition as defined above, and a method for combating fungus at a locus, which comprises treating the locus, which may be for example plants subject to or subjected to fungal attack, seeds of such plants or the medium in which such plants are growing or are to be grown, with such a compound or composition.

The present invention is of wide applicability in the protection of crop and ornamental plants against fungal attack. Typical crops which may be protected include vines, grain crops such as wheat and barley, rice, sugar beet, top fruit, peanuts, potatoes, vegetables and tomatoes. The duration of the protection is normally dependent on the individual compound selected, and also a variety of external factors, such as climate, whose impact is normally mitigated by the use of a suitable formulation.

The following examples further illustrate the present invention. It should be understood, however, that the invention is not limited solely to the particular examples given below.

EXAMPLE 1

Preparation of 2-acetoxy-5-bromo-6,6'-dimethyl-2', 3',4'-trimethoxybenzophenone

1A Ethyl 5-bromo-6-methyl-2-hydroxybenzoate

A mixture of bromine (5.05 ml, 0.099 mol) and acetic acid (15 ml) is added to a mixture of ethyl 6-methyl-2-hydroxybenzoate (17.05 g, 0.095 mol), and acetic acid (15 ml) at a temperature of 20° C. The reaction mixture is stirred at room temperature for 1 hour. The reaction mixture is diluted with water and ethyl acetate. The organic phase is washed with water twice, concentrated in vacuo and the residue is purified by flash chromatography (petrol ethers-:ethyl acetate, 98:2 v/v) yielding the pure product as a yellow oil, 21.7 g, (88.2%).

1B 2-Hydroxy-5-bromo-6-methylbenzoic acid

A mixture of 1A (20.2 g, 0.078 mol), ethanol (150 ml) and an aqueous sodium hydroxide (12 g, 0.3 mol in 100 ml water) is heated under reflux with stirring for 16 hours. The reaction mixture is cooled to room temperature, diluted with water (600 ml) and acidified with concentrated hydrochloric acid. The precipitate is collected and washed with water yielding 18.45 g (100%) white crystals with a melting point of 163–165° C.

1C 2-Acetoxy-5-bromo-6-methylbenzoic acid

A mixture of 1B (6.93 g, 30 mmol), acetic anhydride (3.5 ml, 36 mmol) and pyridine (15 ml) is heated under reflux with stirring for 16 hours. The reaction mixture is diluted with water and ethyl acetate. The organic phase is acidified with dilute hydrochloric acid and washed with water twice. The organic phase is concentrated in vacuo and the residue is purified by flash chromatography (dichloromethane:methanol, 9:1 v/v) yielding the pure product as a yellow oil, 7.4 g, (90.3%).

1D 2-Acetoxy-5-bromo-6,6'-dimethyl-2', 3', 4'-trimethoxy-benzophenone

A mixture of 1C (6.83 g, 25 mmol), 3,4,5-trimethoxytoluene (4.56 g; 25 mmol), $P_2O_5$ (15.0 g) and dichloromethane (100 ml) is stirred at room temperature for 16 hours. Subsequently, the dichloromethane is distilled off and the residue is diluted with water and ethyl acetate. The organic phase is washed with water and concentrated. The residue is purified by preparative HPLC with acetonitrile-:water 9:1 as eluent yielding the pure product as a yellow oil, 1.1 g, (10.1%).

EXAMPLE 2

Preparation of 5-bromo-6,6'-dimethyl-2-hydroxy-2', 3',4'-trimethoxybenzophenone

A mixture of 1D (0.7 g, 1.6 mmol), potassium carbonate (0.7 g), methanol (10 ml) and water (5 ml) is stirred at room temperature for 20 hours. The reaction mixture is poured into water and extracted with diisopropylether. The organic phase is separated and concentrated. The pure product is obtained as a yellow solid, 0.48 g (75.9%), mp. 119–120° C.

EXAMPLE 3

Preparation of 6,6'-dimethyl-2-hydroxy-2',3',4'-trimethoxy-benzophenone 3A 2-Methyl-6-pivaloyloxybenoic acid A mixture of 2-hydroxy-6-methylbenoic acid (5.9 g, 38.8 mmol), pivaloylanhydride (8.6 ml, 42.6 mmol), a trace of p-toluenesulfonic acid and toluene (50 ml) is heated to 100° C. with stirring for 16 hours. The reaction mixture is extracted with water. The organic phase is dried and concentrated in vacuo and the residue is re-crystallized from (petrolether:ethyl acetate, 95:5 v/v) yielding the pure product as a white crystals, 3.6 g, (39.3%).

3B 6,6'-dimethyl-2-pivaloyloxy-2',3',4'-trimethoxy-benzophenone

A mixture of 3A (3.6 g, 15.3 mmol), 3,4,5-trimethoxytoluene (2.78 g; 15.3 mmol), $P_2O_5$ (9.0 g) and dichloromethane (80 ml) is stirred at room temperature for 16 hours. Subsequently, the dichloromethane is distilled off and the residue is diluted with water and ethyl acetate. The organic phase is washed with water and concentrated. The residue is purified by flash chromatography with petrolether-:ethyl acetate 95:5 as eluent yielding the pure product as a yellow oil, 1.42 g, (23.2%).

3C 6,6'-dimethyl-2-hydroxy-2',3',4'-trimethoxy-benzophenone

A mixture of 3B (1.42 g, 3.6 mmol), potassium carbonate (1.5 g), methanol (30 ml) and water (10 ml) is stirred at room temperature for 16 hours. The reaction mixture is poured into water, acidified and extracted with diisopropylether. The organic phase is separated and concentrated. The pure product is obtained as a yellow solid, 0.75 g (65.8%), mp. 82–84° C.

EXAMPLES 4–49

Using essentially the same procedures described hereinabove for Examples 1 to 3 and employing standard derivatization techniques where appropriate, the following compounds are prepared and shown in Table I:

TABLE I

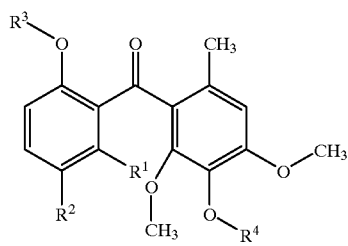

| Example | $R^1$ | $R^2$ | $R^3$ | $R^4$ | |
|---|---|---|---|---|---|
| 4 | methyl | H | acetyl | methyl | |
| 5 | methyl | Cl | acetyl | methyl | |
| 6 | methyl | Cl | H | methyl | m.p. 113–114° C. |
| 7 | methyl | $NO_2$ | acetyl | methyl | |
| 8 | methyl | $NO_2$ | H | methyl | |
| 9 | methyl | $CF_3$ | acetyl | methyl | |
| 10 | methyl | $CF_3$ | H | methyl | |

TABLE I-continued

| Example | $R^1$ | $R^2$ | $R^3$ | $R^4$ |
|---|---|---|---|---|
| 11 | methyl | $CH_3O$ | acetyl | methyl |
| 12 | methyl | $CH_3O$ | H | methyl |
| 13 | methyl | I | acetyl | methyl |
| 14 | methyl | I | H | methyl |
| 15 | methyl | Br | n-propionyl | methyl |
| 16 | methyl | Br | n-butyryl | methyl |
| 17 | methyl | Br | n-pentanoyl | methyl |
| 18 | methyl | Br | pivaloyl | methyl |
| 19 | methyl | Br | benzoyl | methyl |
| 20 | Cl | methyl | acetyl | methyl |
| 21 | Cl | methyl | pivaloyl | methyl |
| 22 | Cl | methyl | H | methyl |
| 23 | Cl | Br | acetyl | methyl |
| 24 | Cl | Br | pivaloyl | methyl |
| 25 | Cl | Br | H | methyl |
| 26 | Cl | H | acetyl | methyl |
| 27 | Cl | H | H | methyl |
| 28 | Cl | Cl | acetyl | methyl |
| 29 | Cl | Cl | H | methyl |
| 30 | Cl | methyl | H | pentyl |
| 31 | methyl | Br | H | ethyl |
| 32 | methyl | Br | H | propyl |
| 33 | methyl | Br | H | butyl |
| 34 | methyl | Br | H | pentyl |
| 35 | methyl | Br | H | hexyl |
| 36 | methyl | Br | H | heptyl |
| 37 | methyl | Br | acetyl | ethyl |
| 38 | methyl | Br | acetyl | propyl |
| 39 | methyl | Br | acetyl | butyl |
| 40 | methyl | Br | acetyl | pentyl |
| 41 | methyl | Br | acetyl | hexyl |
| 42 | methyl | Br | acetyl | heptyl |
| 43 | methyl | Br | pivaloyl | ethyl |
| 44 | methyl | Br | pivaloyl | propyl |
| 45 | methyl | Br | pivaloyl | butyl |
| 46 | methyl | Br | pivaloyl | pentyl |
| 47 | methyl | Br | pivaloyl | hexyl |
| 48 | methyl | Br | pivaloyl | heptyl |
| 49 | —CH=CH—CH=CH— | | H | methyl |

EXAMPLE 50

Preparation of 2-hydroxy-5-bromo-6,6'-dimethyl-2', 3',4'-trimethoxybenzophenone 50A 2-Pivaloyloxy-5-bromo-6-methylbenzoic acid A mixture of 1B (6.45 g, 28 mmol), pivaloylchloride (3.62 g, 30 mmol), tetrahydrofuran (60 ml) and pyridine (2.45 ml) is stirred at room temperature for 16 hours. The reaction mixture is diluted with water and ethyl acetate. The organic phase is washed with water twice. The organic phase is concentrated in vacuo and the residue is re-crystallized from petrol ethers/diisopropylether (9:1 v/v) yielding the pure product as a white crystals, 6.3 g, (71.6%), mp. 144–145° C.

50B 5-Bromo-6,6'-dimethyl-2-pivaloyloxy-2',3',4'-trimethoxybenzophenone

A mixture of 50A (6.3 g, 20 mmol), 3,4,5-trimethoxytoluene (3.83 g; 21 mmol), $P_2O_5$ (12.0 g) and dichloromethane (100 ml) is stirred at room temperature for 16 hours. Subsequently, the dichloromethane is distilled off and the residue is diluted with water and ethyl acetate. The organic phase is washed with water and concentrated. The residue is purified by flash chromatography with petrol ethers/ethyl acetate (9:1 v/v) as eluent yielding the pure product as white crystals, 5.58 g, (58.2%).

50C 5-Bromo-6,6'-dimethyl-2-hydroxy-2', 3', 4'-trimethoxy-benzophenone

A mixture of 50B (5.1 g, 10.6 mmol), sodium carbonate (3.65 g), methanol (100 ml) and water (30 ml) is heated to reflux with stirring for 1 hour. The reaction mixture is diluted with water and extracted with ethyl acetate. The organic phase is separated and concentrated. The residue is recrystallized from petrol ethers/ethyl acetate (95:5 v/v) The pure product is obtained as yellowish crystals, 3.70 g (88.3%), mp. 119–120° C.

Biological Investigations

Curative and Residual Fungicidal Activity

Wheat Powdery Mildew (WPM):

HOST: Wheat (*Triticum aestivum* L.) variety Kanzler

PATHOGEN: *Blumeria* (*Erysiphe*) *graminis* DC. f.sp. *tritici* E. Marchal

TEST PROCEDURE:

1. Wheat seed (approximately 8–10/pot) is planted in 6 cm diameter plastic pots and maintained in the greenhouse.
2. When the primary leaf (wheat) is fully expanded, formulated test compounds are sprayed with a single nozzle overhead track sprayer at a rate of 200 l/ha. Plants are then allowed to air-dry.
3. Inoculation precedes treatment by 3 days in the case of curative evaluations and follows treatment by 4 or 5 days in case of residual evaluations. For inoculation, plants are set up on greenhouse benches with bottom watering mats and inoculated by dusting them with conidia from powdery mildew infected plants (stock cultures at an age of 10–14 days). Between inoculation and treatment for curative evaluations and between treatment and inoculation for residual evaluations, plants are maintained in the greenhouse with bottom watering.
4. Disease on the primary leaf as percent leaf area with disease symptoms/signs is evaluated about 7 days after inoculation. In the case of wheat, the tips and bases of the leaves are excluded from the evaluation.

Percent disease control is then calculated by the following formula:

$$\% \text{ disease control} = 100 - \frac{\% \text{ infection in treated plants}}{\% \text{ infection in untreated plants}} \times 100$$

FORMULATION, REFERENCE COMPOUNDS AND CONTROLS

1. Technical compounds are formulated in a solvent/surfactant system consisting of 5% acetone and 0.05% Tween 20 in deionized water. Compounds are dissolved in acetone prior to addition of the water; the Tween 20 can be added through either the acetone or the water. Dilutions are made using the solvent/surfactant system. Formulated compounds are prepared using deionized water.
2. Two kinds of controls are included:
   Plants treated with the solvent/surfactant solution and inoculated (Solvent Blank).
   Untreated plants which are inoculated (Inoculated Control).

The results of this evaluation are shown in Table III:

TABLE III

Curative and Residual Fungicidal activity of 2-hydroxy-benzophenones

| Disease Test | Rate (ppm) | Disease control (% efficacy) Example | | |
|---|---|---|---|---|
| | | 1 | 2 | 6 |
| WPM 3 da C | 125 | 55 | 59 | 43 |
| | 25 | 49 | 53 | 33 |
| | 5 | 33 | 37 | 16 |
| | 1 | 17 | 23 | 11 |
| | 0.2 | 2 | 13 | n.t. |
| WPM 4/5 da R | 125 | 100 | 100 | n.t. |
| | 25 | 100 | 100 | 100 |
| | 5 | 98 | 100 | 85 |
| | 1 | 84 | 98 | 57 |
| | 0.2 | 53 | 86 | 26 |

3 da C = 3 day curative   Inoculation 3 days BEFORE application
4/5 da R = 4/5 day residual   Inoculation 4 or 5 days AFTER application Comparison Test The fungicidal activity against wheat powdery mildew of the hydroxybenzophenones according to this invention has been compared with a fungicidal benzophenone known from EP 0 727 141 in the following table. Compounds applied to seedling wheat plants using a single-nozzle overhead track sprayer at an application rate of 200 l/ha.

TABLE IV

Curative and Residual Fungicidal activity of a 2-hydroxy-benzophenones compared with a known benzophenone

| Example | Rate [ppm] | WPM | | |
|---|---|---|---|---|
| | | 3 day curative Antisporulation effect* | 3 day curative % disease control | 4 day residual % disease control |
| 2 | 25 | +++ | 40 | 100 |
| | 5 | + | 22 | 78 |
| | 1 | + | 10 | 52 |
| standard** | 25 | + | 6 | 92 |
| | 5 | o | 3 | 47 |
| | 1 | o | 0 | 15 |

*Scale for antisporulation effect:
+++ = complete (no spore release)
++ = moderate
+ = slight
o = none
**standard: 2'-n-butyloxy-2,6-dichloro-3', 5'-dimethoxy-6'-methyl-benzophenone

What is claimed is:

1. A compound of formula I:

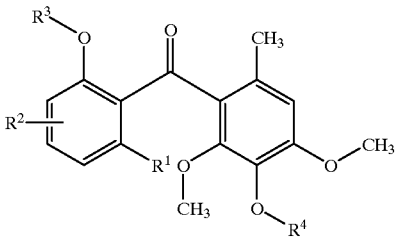

(I)

wherein
$R^1$ represents a halogen atom or an alkyl or fluoroalkyl group;
$R^2$ represents a hydrogen or halogen atom, or an optionally substituted alkyl or alkoxy group or a nitro group; or
$R^1$ and $R^2$ may be taken together to represent a —CH=CH—CH=CH— group;
$R^3$ represents a hydrogen atom or a protecting group; and
$R^4$ represents an optionally substituted alkyl group.

2. A compound as claimed in claim 1, wherein
$R^1$ represents a chloro atom or a methyl group;
$R^2$ represents a hydrogen, chloro or bromo atom or a methyl or trifluoromethyl group;
$R^3$ represents a hydrogen atom or a $C_{2-6}$ acyl group; and
$R^4$ represents a $C_{1-5}$ alkyl group.

3. A compound of formula IA,

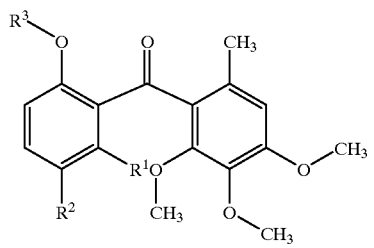

(IA)

in which
$R^1$ represents a chloro atom or a methyl group,
$R^2$ represents a hydrogen, chloro or bromo atom or a methyl group, and
$R^3$ represents a hydrogen atom or an acetyl or pivaloyl group.

4. A compound as claimed in claim 3 being selected from the group consisting of 6,6'-dimethyl-2-hydroxy-2',3',4'-trimethoxy-benzophenone,
6,6'-dimethyl-2-acetoxy-2',3',4'-trimethoxy-benzophenone,
5-bromo-6,6'-dimethyl-2-hydroxy-2',3',4'-trimethoxy-benzophenone,
5-bromo-6,6'-dimethyl-2-acetoxy-2',3',4'-trimethoxy-benzophenone,
5-bromo-6,6'-dimethyl-2-pivaloyloxy-2',3',4'-trimethoxy-benzophenone,
5-chloro-6,6'-dimethyl-2-hydroxy-2',3',4'-trimethoxy-benzophenone,
5-chloro-6,6'-dimethyl-2-acetoxy-2',3',4'-trimethoxy-benzophenone,
5-chloro-6,6'-dimethyl-2-pivaloyloxy-2',3',4'-trimethoxy-benzophenone.

5. A process for the preparation of the compound of claim 1, which comprises the steps of
(a) reacting a compound of formula II,

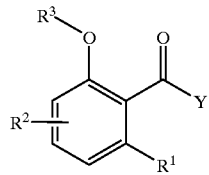

(II)

wherein $R^1$, $R^2$ and $R^3$ have the meaning given above and Y represents a leaving group, with compound of formula III,

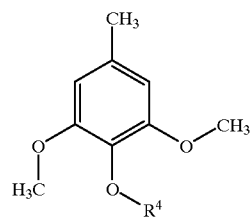

(III)

wherein $R^4$ has the meaning given for claim 1, in the presence of a Lewis acid.

6. A process for the preparation of a compound of formula II as described in claim 5, wherein $R^2$ represents a halogen atom, which comprises
(a) reacting a compound of formula V,

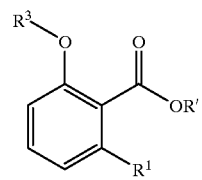

(V)

wherein $R^1$ and $R^3$ have the meaning given for claim 1 and R' represents a hydrogen atom or an alkyl group, with a halogenating agent,
(b) optionally hydrolyzing the resulting halogenated alkyl benzoate (R'=alkyl), and
(c) optionally treating the resulting halogenated benzoic acid with thionyl chloride.

7. A composition which comprises a fungicidally effective amount of at least one compound of claim 1, and a carrier.

8. A method of combating fungus or a fungal plant disease at a locus, which comprises treating the locus with a compound of claim 1.

9. A method of combating fungus or a fungal plant disease at a locus, which comprises treating the locus with the composition of claim 7.

10. The method of claim 8 wherein the fungal plant disease is ascomycetes.

11. The method of claim 9 wherein the fungal plant disease is ascomycetes.

12. The method according to claim 8 wherein the fungus is a member of the subgroup Erysiphales.

13. The method of claim 12 wherein the fungus is selected from *Blumeria (Erysiphe) graminis, Erysiphe cichoracearum, Podosphaera leucotricha* or *Uncinula necator*.

14. The method according to claim 9 wherein the fungus is a member of the subgroup Erysiphales.

15. The method of claim 14 wherein the fungus is selected from *Blumeria (Erysiphe) graminis, (Erysiph) cichoracearum, Podosphaera leucotricha* or *Uncinula necator*.

16. A process for the preparation of a compound of formula II,

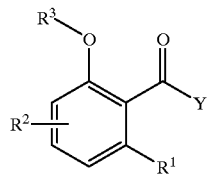

(II)

wherein
R¹ represents a hologen atom or an alkyl or fluoroalkyl group;
R² represents a bromine atom;
R³ represents a hydrogen atom or a protecting group; and
Y represents a hydrogen atom or an alkyl group; which comprises reacting a compound of formula IV,

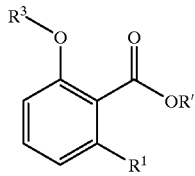

(IV)

wherein R¹ is an alkyl group; R³ is a hydrogen atom or an acetyl group; and R' represents a hydrogen atom, with bromine.

* * * * *